US009681944B2

(12) United States Patent
Zhao (10) Patent No.: US 9,681,944 B2
(45) Date of Patent: *Jun. 20, 2017

(54) ACCOMMODATING INTRAOCULAR LENS PROVIDING PROGRESSIVE POWER CHANGE

(71) Applicant: ABBOTT MEDICAL OPTICS INC., Santa Ana, CA (US)

(72) Inventor: Huawei Zhao, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/979,535

(22) Filed: Dec. 28, 2015

(65) Prior Publication Data

US 2016/0128827 A1    May 12, 2016

Related U.S. Application Data

(62) Division of application No. 14/133,866, filed on Dec. 19, 2013, now Pat. No. 9,220,591.

(60) Provisional application No. 61/740,845, filed on Dec. 21, 2012.

(51) Int. Cl.
*A61F 2/16* (2006.01)

(52) U.S. Cl.
CPC .......... *A61F 2/1618* (2013.01); *A61F 2/1624* (2013.01); *A61F 2/1627* (2013.01); *A61F 2/1635* (2013.01); *A61F 2/1648* (2013.01); A61F 2250/0014 (2013.01); A61F 2250/0018 (2013.01); A61F 2250/0019 (2013.01)

(58) Field of Classification Search
CPC .... A61F 2/1635; A61F 2/1618; A61F 2/1624; A61F 2/1627; A61F 2/1648; A61F 2250/0014
USPC .............................. 623/6.13, 6.28, 6.34, 6.37
See application file for complete search history.

(56) References Cited

U.S. PATENT DOCUMENTS

| 5,089,024 A | 2/1992 | Christie et al. |
| 6,599,317 B1 | 7/2003 | Weinschenk, III |
| 6,638,305 B2 | 10/2003 | Laguette |
| 6,695,880 B1 | 2/2004 | Roffman et al. |
| 7,220,279 B2 | 5/2007 | Nun |
| 2004/0111153 A1 | 6/2004 | Woods et al. |
| 2005/0107873 A1 | 5/2005 | Zhou |

FOREIGN PATENT DOCUMENTS

| WO | 0119290 A1 | 3/2001 |
| WO | 2006023404 A2 | 3/2006 |
| WO | 2009088448 A2 | 7/2009 |
| WO | 2009140080 A2 | 11/2009 |
| WO | 2010045294 A1 | 4/2010 |

OTHER PUBLICATIONS

International Search Report for Application No. PCT/US2013/076370, mailed on Feb. 21, 2014, 10 pages.

*Primary Examiner* — David H Willse
*Assistant Examiner* — Javier Blanco
(74) *Attorney, Agent, or Firm* — Abbott Medical Optics Inc.

(57) ABSTRACT

An accommodating intraocular lens for providing a range of accommodative vision includes a deformable optic. The deformable optic includes a plurality of layers that have a progressively increasing hardness and/or refractive index characteristic from the outermost layer to the innermost layer to provide a range of accommodative power.

5 Claims, 11 Drawing Sheets

ACCOMMODATING INTRAOCULAR LENS PROVIDING PROGRESSIVE POWER CHANGE

CROSS-REFERENCES TO RELATED APPLICATIONS

This application is a divisional application of, and claims priority to, U.S. application Ser. No. 14/133,866 filed on Dec. 19, 2013 which claims priority to U.S. Application No. 61/740,845, filed on Dec. 21, 2012, the entireties of which are hereby incorporated by reference.

BACKGROUND OF THE INVENTION

Field of the Invention

The present invention relates generally to intraocular lenses, and more specifically to intraocular lenses for providing accommodative vision.

Description of the Related Art

Figure 1:
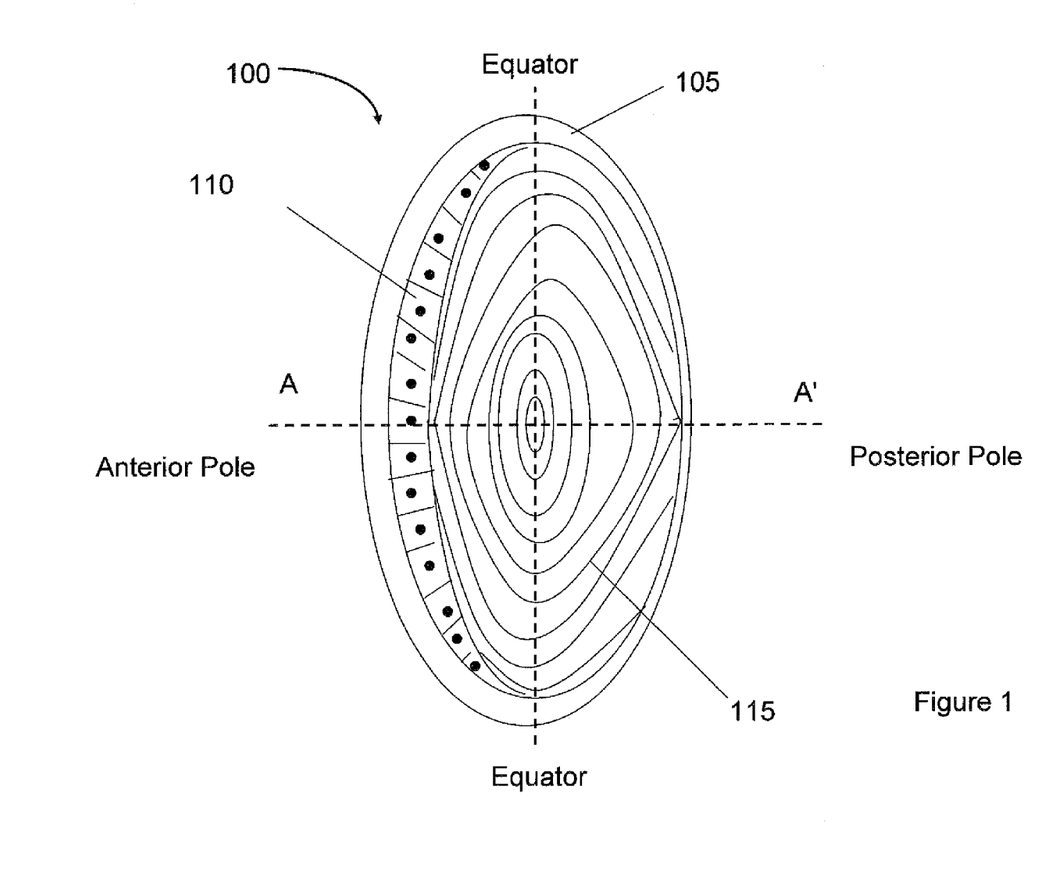
FIG. 1 is a cross-sectional view of a natural crystalline lens.

A human eye includes a transparent crystalline biconvex lens which can focus light from objects over a wide range of distances on the retina. The lens allows the eye to focus on objects at various distances by changing its shape thereby changing its focal length. The ability of the lens to change its shape to adjust focal length is known as accommodation. FIG. 1 is a schematic illustration of a cross-section of the natural crystalline lens 100. The lens 100 is connected to the ciliary body at the periphery of the lens generally in the equatorial plane. The lens 100 has an optical axis A-A' which extends from the anterior pole through the posterior pole. The lens 100 has three main parts: the lens capsule 105, the lens epithelium 110, and the lens fibers 115. The lens capsule 105 forms the outermost layer of the lens 100 and the lens fibers 115 form the bulk of the interior of the lens 100 with the cells of the lens epithelium 110, located between the lens capsule 105 and the outermost layer of lens fibers 115 on the anterior side of the lens.

The lens capsule 105 is an elastic, transparent membrane that completely surrounds the lens. The lens epithelium 110 is located in the anterior portion of the lens between the lens capsule 105 and the lens fibers 115 and is responsible for regulating of the homeostatic functions of the lens. The cells of the lens epithelium 110 also serve as the progenitors for new lens fibers.

The lens fibers 115 are long, thin, transparent cells that are firmly packed within the lens capsule 105. The lens fibers 115 stretch lengthwise from the anterior pole to the posterior pole with the middle of each fiber located on the equator. The lens fibers 115 are arranged in concentric layers rather like the layers of an onion in a cross-sectional view of the lens along a plane perpendicular to the equatorial plane as illustrated in FIG. 1. The lens fibers appear as a honeycomb a cross-sectional view of the lens along the equatorial plane (not shown).

The refractive index of the lens fibers 115 increases progressively from the outermost lens fibers 115 that are adjacent to the lens capsule having a refractive index of approximately 1.38 to the inner most lens fibers having a refractive index of approximately 1.41. The refractive index gradient is advantageous in enhancing the optical power of the lens.

A human eye can suffer diseases that impair a patient's vision. For instance, a cataract may increase the opacity of the lens, causing blindness. To restore the patient's vision, the opaque lens may be surgically removed and replaced with an artificial intraocular lens, or IOL. An artificial IOL may also be implanted to treat presbyopia or for other elective ocular surgical procedures.

The artificial IOL can be an accommodating IOL, which can adjust its axial position and/or shape to vary the optical power within a range in response to muscle action in the eye. As a result, the patient can focus on objects in a range of distances from the eye, rather than at one or more discrete distances.

SUMMARY OF THE INVENTION

The systems, methods and devices of the disclosure each have several innovative aspects, no single one of which is solely responsible for the desirable attributes disclosed herein.

Embodiments disclosed herein are directed to devices and methods for providing accommodative vision. It some embodiments, it would be desirable to have an accommodating IOL that mimics the natural lens.

In one aspect, an intraocular lens is provided that comprises an adjustable optic adapted to focus light on the retina when disposed in the eye. In various implementations of the IOL, the adjustable optic can comprise an elastic material that can be deformed by ocular forces. Various implementations of the accommodating IOL disclosed herein are configured to occupy a substantial portion of the volume of an evacuated capsular bag. The implementations of the accommodating IOLs disclosed herein include a plurality of elastic layers, each layer contributing to the total optical power of the IOL in the accommodated or unaccommodated state. The accommodating IOL has progressively changing refractive index and/or hardness characteristic. In one embodiment, the outer layers that are adjacent to the inner surfaces of the evacuated capsular bag have a refractive index and/or hardness characteristic lower than refractive index and/or hardness characteristic of the inner layers, such that the refractive index and/or hardness characteristic progressively increases from the outer to inner layers. In another embodiment, the refractive index and/or hardness characteristic can progressively decrease from the outer to inner layers. In another embodiment, the refractive index and/or hardness characteristic may initially increase and then decrease moving from the outer to inner layers. In another embodiment, the refractive index and/or hardness characteristic may initially decrease and then increase moving from the outer to inner layers.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Embodiments disclosed herein may be better understood from the following detailed description when read in conjunction with the accompanying drawings. Such embodiments, which are for illustrative purposes only, depict novel and non-obvious aspects of the inventions. The drawings include the following figures.

DETAILED DESCRIPTION OF THE PREFERRED EMBODIMENT

In a healthy human eye, the natural lens 100 illustrated in FIG. 1 a structure known as the capsular bag. During natural accommodation, the capsular bag is acted on by a ciliary muscle and zonular fibers (also known as zonules) in the eye, which can pull on the capsular bag to change its shape. The motion of the capsular bag generally deforms the natural lens in order to change its power and/or the location of the lens, so that the eye can focus on objects at varying distances away from the eye in a process known as accommodation.

Embodiments described herein are directed to intraocular lenses that advantageously use ocular forces, such as those produced by the ciliary muscle, zonules, and/or capsular bag, to change the shape of the lens optic. Such an accommodating lens may produce vastly improved vision over a lens with a fixed power and location that does not accommodate. However, the term "ocular force" does not necessarily refer to forces produced by ciliary muscle, zonules, and/or capsular bag. As used herein the term "ocular force" is a broad term that includes a force produced by or in the eye that is sufficient to provide accommodation in the eye of a healthy human subject.

Figure 2A:
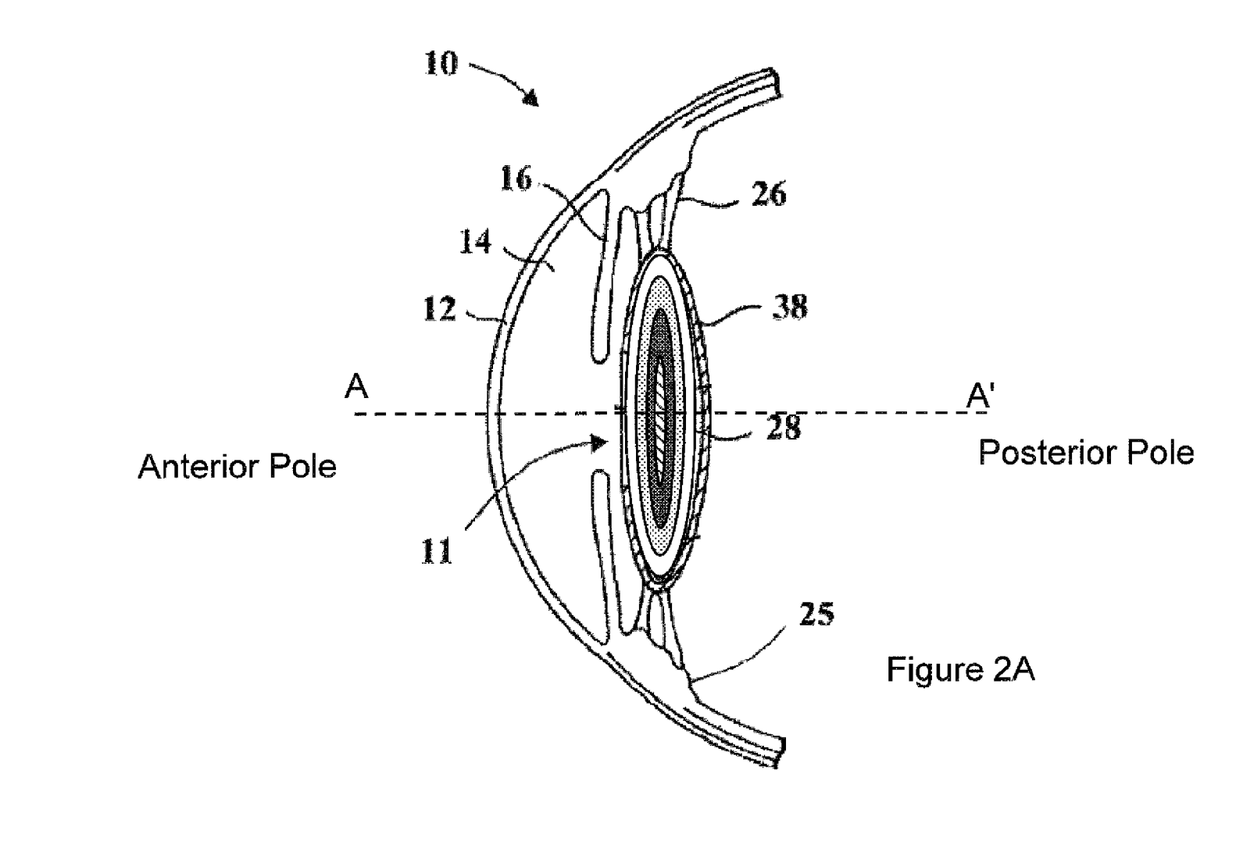
FIG. 2A is a cross-sectional view of the human eye implanted with an implementation of an intraocular lens which includes a plurality of layers with varying, e.g., progressively increasing hardness and/or refractive characteristic.

FIG. 2A shows a human eye 10, after an accommodating intraocular lens 11 is implanted. Prior to surgery, the natural lens 100 occupies essentially the entire interior of the capsular bag 38. During surgery the natural lens 100 is removed by a process by making an incision through the capsular bag 38 (called a capsulorhexis). After the capsulorhexis is formed, the contents of the capsular bag 38 are generally removed, or evacuated. A large portion of the capsular bag 38 can be left intact. The intraocular lens 11 is implanted in the evacuated capsular bag 38. Similar to the natural lens 100, the implanted accommodating intraocular lens 11 can also be configured to occupy a substantial portion of the volume of the evacuated capsular bag 38.

Light enters from the eye 10 from the left in FIG. 2A and passes through the cornea 12, the anterior chamber 14, the pupil (defined by the inner edge of the iris 16), and impinges on the intraocular lens 11. After passing through the intraocular lens 11, light exits the posterior wall of the capsular bag 38, and strikes the retina, which detects the light and converts it to a signal transmitted through the optic nerve to the brain.

A well-corrected eye forms an image at the retina. If the intraocular lens 11 has too much or too little power, the image shifts axially along the optical axis A-A' away from the retina, toward or away from the lens 11. Note that the total power of the eye (e.g., including the combined power of cornea 12 and the intraocular lens 11) required to focus on a close or near object is more than the power required to focus on a distant or far object. The difference between the "near power" and "far power" is known typically as the range of accommodation or the add power. A typical range of accommodation or add power is about 2 to 4 diopters, but may be significantly larger for younger human subjects.

The intraocular lens 11 may be designed so that its relaxed or natural state is the "far" or "distant" condition (sometimes referred to as a "disaccommodative biased" intraocular lens), the "near" condition (an "accommodative biased" intraocular lens), or some condition in between the two. As used herein, the terms "natural state", "natural configuration", "relaxed state", and "relaxed condition" can refer to a condition of an intraocular lens in which no external forces (e.g., ocular forces from the ciliary muscle, zonules, or capsular bag) are acting upon the intraocular lens 11.

The capsular bag 38 is acted upon by the ciliary muscle 25 via the zonules 26, which distort the capsular bag 38 by stretching it radially in a relatively thick band about its equator. Experimentally, it is found that the ciliary muscle 25 and/or the zonules 26 typically exert a total force of up to about 10 grams of force, which is generally distributed uniformly around an equatorial region of the capsular bag 38. In some patients, non-uniform forces may be applied to the capsular bag 38, for example, due to damage of the zonules, which can cause astigmatism or other optical aberrations.

Although the range of ocular force may vary from patient to patient, the range of accommodation for each subject is generally limited by the total ocular force available. Therefore, it is generally preferred that the intraocular lens 11 be configured to vary its power over the full range of accommodation in response to this limited range of ocular forces (e.g., to provide up to 3 Diopters or 4 Diopters or more of accommodative power). In other words, it is desirable to have a relatively large change in power for a relatively small driving force. Alternatively, the effective range of accommodation may be increased by incorporating a lens having a multifocal or extended depth-of-focus configuration.

The intraocular lens 11 generally has an optic 28 made of a transparent, deformable and/or elastic material. In various implementations, the intraocular lens 11 can include a haptic that is configured to hold the optic 28 in place and to mechanically transfers forces from the eye (e.g., from the capsular bag 38, the ciliary muscle 25 or the zonules 26) to the optic 28. In some implementations, the optic 28 may be disposed to directly contact the inner surfaces of the capsular bag 38 as illustrated in FIG. 2A. In such implementations, accommodation of the optic 28 can be achieved by the forces exerted by the capsular bag 38.

When the eye 10 is focused on a relatively close object, the ciliary muscle 25 is compressed, which causes the zonules 26 to relax and allow the equatorial region of the capsular bag 38 to contract. The capsular bag 38 in this state is thicker at its center and has more steeply curved sides. In some implementations, the contraction of the capsular bag can compress the edges of the optic 28 such that the radii of curvature of one or both of the anterior or posterior lens surfaces, or of any one or more internal layers thereof, can decrease, and/or the lens can become thicker in its center and/or the lens can move axially. As a result, the power of the lens 11 is relatively high and an image of the relatively close object can be formed at the retina. Note that if the lens could not accommodate, the image of the relatively close object would, for an emmetropic eye, be located behind the retina, and would appear blurred. Also, if the eye has aberrations such as astigmatism, uniform power in all diameters or segments of the lens would not produce satisfactory vision. For some diameters or segments, light would focus at the retina and for others light would focus behind or in front of the retina.

When the eye 10 is focused on a relatively distant object, the zonules 26 are retracted and the shape of the capsular bag 38 is thinner at its center and has less steeply curved sides. Accordingly, a flattening force is applied to the optic 28, e.g., a radially outward force generally in a plane perpendicular to the optical axis A-A' of the optic 28. In some embodiments, retraction of the zonules 28 causes opposed compressive forces on the anterior and/or posterior faces of the optic 28 such that the optic 28 is flattened. This reduces the lens power due to the lengthening of the radii of curvature of the anterior and/or posterior surfaces of the optic, or of any one or more internal layers thereof, thus, placing the image of the relatively distant object at the retina.

For both the "near" case and the "far" case, the accommodating intraocular lens 11 deforms and changes shape in response to the ciliary muscle 25 and/or to the distortion of the capsular bag 38. For the "near" object, the capsular bag may relax, imparting a compressive force to the edges of the optic 28 such that the optic 28 has an increased thickness at its center and more steeply curved anterior and/or posterior surface. As a result, the lens power increases. For the "far" object, the capsular bag 38 may be stretched, imparting a pulling force on the edges of the optic 28 thereby decreasing the thickness of the optic 28 at its center and less steeply curving (e.g., lengthening one or both radius of curvature) its anterior and/or posterior surface, or of any one or more internal layers thereof. As a result, the lens power decreases.

The specific degrees of change in curvature of the anterior and posterior faces depend on the nominal curvatures. Although the optic 28 is drawn as bi-convex, it may be plano-convex, meniscus or other lens shapes in other embodiments. In all of these cases, the optic 28 is compressed and/or expanded by forces from the capsular bag 38. In addition, there may be some axial movement of the optic 28. In various embodiments, the optic 28 can be configured such that it deforms symmetrically in response to the forces exerted by the capsular bag 38. In alternate embodiments, the optic 28 may be configured such that it deforms asymmetrically in response to the forces exerted by the capsular bag 38. For example, in some implementations, the portion of the optic 28 above the optical axis A-A' may deform to a greater extend than the portion of the optic 28 below the optical axis A-A'.

Figure 2B:
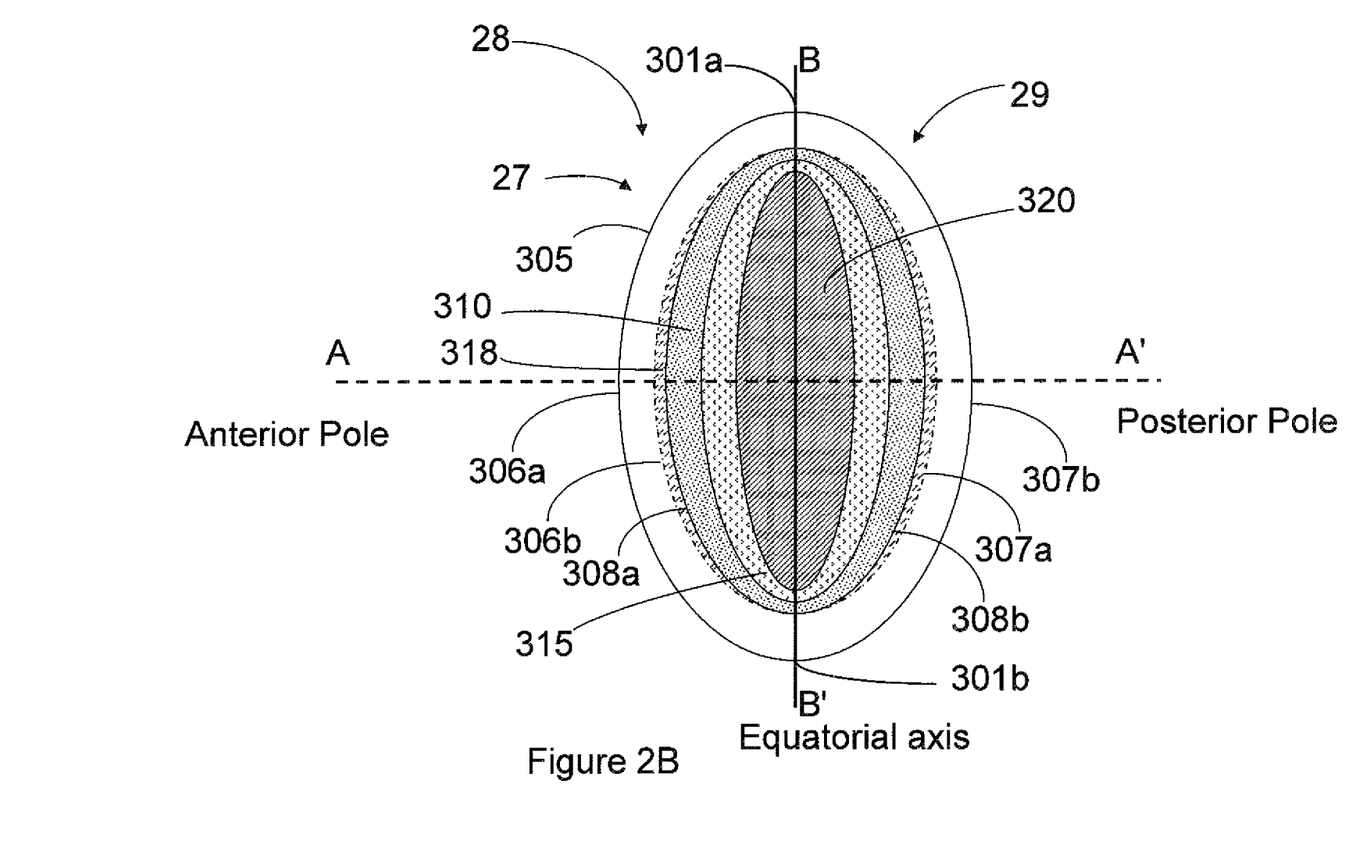
FIG. 2B is a detailed cross-sectional view of an implementation of the optic of the intraocular lens illustrated in FIG. 2A.

FIG. 2B is a detailed cross-sectional view of an implementation of the optic 28 of the intraocular lens illustrated in FIG. 2A. The optic 28 is configured to occupy a substantial portion of the evacuated capsular bag 38. For example, the optic 28 can occupy the entire volume of the evacuated capsular bag 38. In another example, the optic 28 can occupy approximately 50%-90% of the volume of the evacuated capsular bag 38. Accordingly, the optic 28 can have dimensions that are similar to the dimensions of the natural lens. The optic 28 has an optical axis A-A' extending from the anterior pole to the posterior pole. The optic 28 extends laterally in an equatorial plane that includes the equatorial axis B-B'. The equatorial plane divides the optic 28 into an anterior portion 27 and a posterior portion 29. When disposed in the eye 10, the optic 28 can be compressed or stretched in the equatorial plane containing the axis B-B' due to forces exerted by the capsular bag to increase and/or decrease the distance of the anterior portion 27 and/or the posterior portion 29 from the equatorial plane containing the axis B-B' to provide accommodation. In some places below, the phrase "equatorial axis B-B'" is used as shorthand for the equatorial plane, which extends through an anterior-posterior center-point of apices 301a and 301b of the optic 28 seen at the top and bottom of the cross-section of FIG. 2B.

In one implementation, the optic 28 has at least some symmetry about the equatorial plane containing the axis B-B', e.g., with the anterior and posterior portions 27, 29 having substantially the same volume and/or substantially the same dimensions from the equatorial plane containing the axis B-B' to the anterior or posterior surface of the optic 28.

The optic 28 illustrated in FIG. 2B includes a plurality of layers 305, 310, 315 and 320. Although only four layers are shown, the optic 28 can include more or less than four layers. For example, the optic 28 can include five, ten, twenty, fifty, a hundred or a thousand or more layers. In some implementations, the optic 28 can have three or two layers. The number of layers included in the optic 28 can depend on a number of factors including but not limited to the range of accommodative power to be provided, the condition of the eye to be treated, the age and the health of the individual in which the lens is implanted and the cost of the lens. Each layer can have a thickness between approximately 0.01 mm and 1.1 mm and preferably between 0.1 mm and 0.3 mm. Each layer can include an optical grade bio-compatible materials such as, for example, various silicones, acrylics with or without water content, siloxane, etc. Layers may also be liquid or air filled.

The outermost layer 305 of the optic 28 can be divided into an anterior region having an anterior outer surface 306a and an anterior inner surface 306b and a posterior region having a posterior inner surface 307a and a posterior outer surface 307b. The anterior region of the outermost layer 305 is disposed forward of the equatorial plane containing the axis B-B' proximate to anterior portion of the eye and the posterior region of the outermost layer 305 is disposed rearward of the axis B-B' proximate to posterior portion of the eye. As seen from FIG. 2B, the anterior region and the posterior region of the outermost layer 305 are joined in the equatorial zone about the equatorial axis B-B'. In various implementations, the anterior region and the posterior region of the outermost layer 305 can be joined together in the equatorial zone by a smooth and continuous surface that includes the apices 301a and 301b. When the optic 28 is disposed in the eye, the anterior outer surface 306a is adjacent to, e.g., in continuous contact with, the anterior inner surface of the evacuated capsular bag and the posterior outer surface 307b is adjacent to, e.g., in continuous contact with, the posterior inner surface of the evacuated capsular bag. In various implementations, the anterior inner surface of the evacuated capsular bag can be in contact with the anterior outer surface 306a of the outermost layer 305 and/or the posterior inner surface of the evacuated capsular bag can be in contact with the posterior outer surface 307b of the outermost layer 305.

The first inner layer 310 of the optic 28 can be divided into an anterior zone disposed forward of the equatorial axis B-B' and a posterior zone disposed rearward of the equatorial axis B-B'. The anterior surface of the anterior zone of the first inner layer 310 is adjacent to, e.g., in continuous contact with, the anterior inner surface 306b of the outermost layer 305 and the posterior surface of the posterior zone of the first inner layer 310 is adjacent to, e.g., in continuous contact with, the posterior inner surface 307a of the outermost layer 305. In various implementations, the anterior surface of the anterior zone of the first inner layer 310 can be in at least partial contact with the anterior inner surface 306b of the outermost layer 305 and/or the posterior surface of the posterior zone of the first inner layer 310 can be in at least partial contact with the posterior inner surface 307a of the outermost layer 305. In various implementations, one or more intervening layers (e.g intervening layer 318) can be disposed between the surfaces 306b and 308a which is the anterior outer surface of the first inner layer 310 and between the surface 307a and the surface 308b which is the posterior outer surface of the first inner layer 310. The intervening layers can be configured to enhance movement of the adjacent surfaces 306b, 308a and/or the adjacent surfaces 307a, 308b. The enhanced movement can correspond to greater accommodative response, e.g., greater amount of add power per unit of applied ocular force. In one example, a layer of gas (for example, air) or liquid (for example, water or saline) may be disposed between the anterior region of the outermost layer 305 and the anterior zone of the first inner layer 310 (for example, intervening layer 310 can include gas or liquid) and/or the posterior region of the outermost layer 305 and the posterior zone of the first inner layer 310.

The second inner layer 315 of the optic 28 can also be divided into an anterior zone disposed forward of the equatorial plane including the axis B-B' and a posterior zone disposed rearward of the equatorial plane including the axis B-B'. The second inner layer 315 is disposed between the anterior and posterior zones of the first inner layer 310. In various implementations, the second inner layer 315 can be disposed such that the anterior zone of the second inner layer 315 is in contact with, or otherwise disposed adjacent to, the anterior zone of the first inner layer 310 and/or the posterior zone of the second inner layer 315 is in contact with, or otherwise disposed adjacent to, the posterior zone of the first inner layer 310. In alternate implementations, a layer of gas (for example, air) or liquid (for example, water or saline) may be disposed between the anterior zone of the first inner layer 310 and the anterior zone of the second inner layer 315 and/or the posterior zone of the first inner layer 310 and the posterior zone of the second inner layer 315. The gas or liquid layer are examples of intervening layers that can enhance performance of the optic 28, e.g., increase in add power per unit ocular force.

The innermost layer 320 of the optic 28 is disposed between the anterior zone and the posterior zone of the second inner layer 315. The innermost layer 320 can include an anterior portion disposed forward of the equatorial axis B-B' and a posterior portion disposed rearward of the equatorial axis B-B'. In various implementations, the anterior portion of the innermost layer 320 can be in contact with, or otherwise disposed adjacent to, the anterior zone of the second inner layer 315 and/or the posterior portion of the innermost layer 320 can be in contact with, or otherwise disposed adjacent to, the posterior zone of the second inner layer 315. In alternate implementations, a layer of gas (for example, air) or liquid (for example, water or saline) may be disposed between the anterior zone of the inner most layer 320 and the anterior zone of the second inner layer 315 and/or the posterior zone of the inner most layer 320 and the posterior zone of the second inner layer 315. As discussed above, the gas or liquid layer are examples of accommodative performance enhancing structures that can be employed in this an interface between these layers.

During accommodation, the optic 28 is deformed by the ocular forces exerted by the capsular bag. The ocular forces exerted by the capsular may be more concentrated in the equatorial zone disposed around the equatorial axis B-B'. In response to the ocular forces the plurality of layers 305, 310, 315 and/or 320 may be compressed toward the axis A-A' or pulled/extended in a direction away from the axis A-A' in the equatorial plane containing the axis B-B' to deform the optic 28 to provide a range of accommodative powers. In various implementations, each layer 305, 310, 315 and/or 320 may be successively deformed by progressively increasing ocular force. For example, when the ocular force exerted by the capsular bag is sufficiently low only the outermost layer 305 may be compressed while the inner layer 310, 315 and 320 remain substantially undeformed. Subsequently, as the ocular forces increase, the first inner layer 310 is deformed while the inner layers 315 and 320 remain substantially underformed. As the ocular forces further increase, the second inner layer 315 is deformed while the innermost layer 320 remains substantially underformed. The optic 28 can have a base power in the unaccommodated or undeformed state. During accommodation each layer can contribute an add power to the base power to provide the required optical power. In various implementations, in the fully accommodated state (for example, when the applied ocular force is greatest), each layer can contribute 1 diopter of add power. In other implementations, in the fully accommodated state (for example, when the applied ocular force is greatest), each layer toward the outer can contributes 1 diopter of add power. In various implementations, the innermost layer 320 may remain undeformed in the fully accommodated state.

Figure 2C:
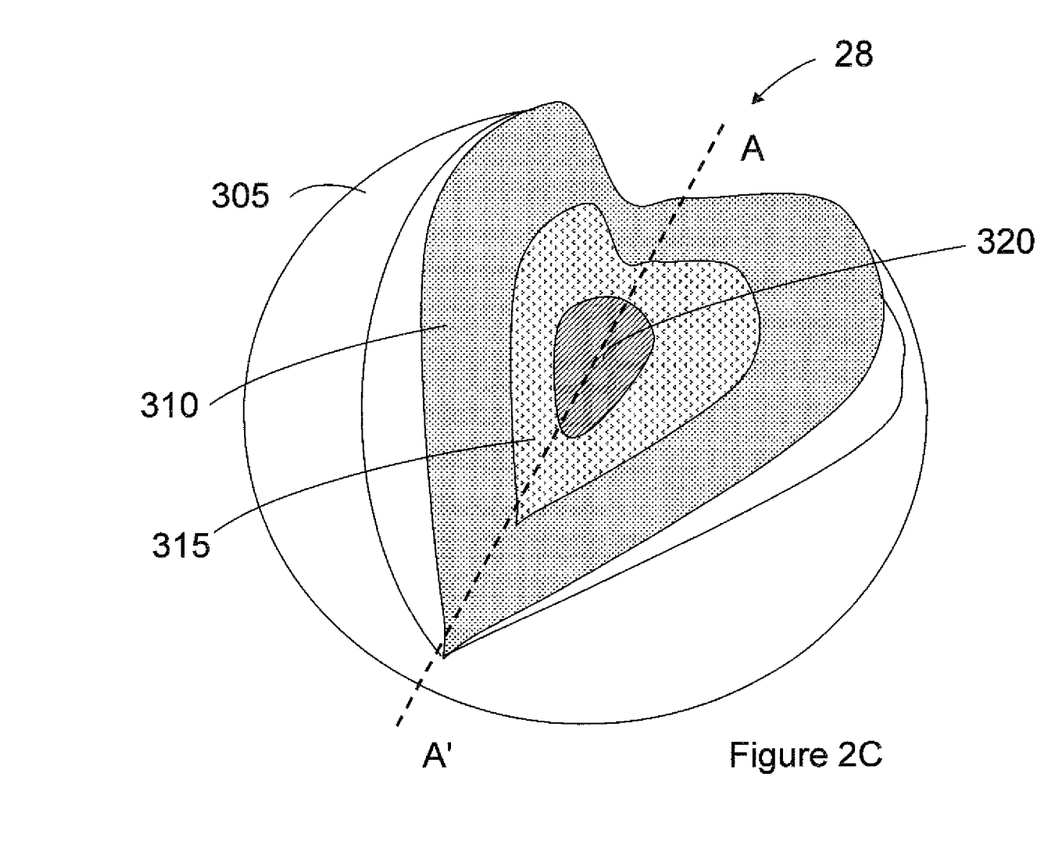
FIG. 2C is a perspective cut away view of the optic illustrated in FIG. 2B.

The structure of the optic 28 illustrated in FIG. 2B and described above closely mimics the structure of the natural lens 100. At least some of the layers 305, 310, 315 and 320 can be provide focusing and accommodating benefit similar to the lens fibers 115 discussed above. Similar to the lens fibers 115, the layers 305, 310, 315 and 320 can stretch lengthwise from the anterior pole to the posterior pole with the middle of each layer located on the equator. The portions of the layers 305, 310, 315 at the apices 301a and 301b can be extended in the equatorial plane, resulting in a thinning along the axis A-A'. Such thinning can correspond to a lessening of the power of the optic 28. The portions of the layers 305, 310, 315 at the apices 301a and 301b can move toward each other causing a bulging of the optic 28. Bulging of the optic can correspond to a increase in the power of the optic 28. As seen from the perspective view of the optic 28 illustrated in FIG. 2C, each layer is arranged concentrically rather like the layers of an onion.

Similar to the lens fibers 115, the hardness and/or the refractive index characteristics the lens 28 can vary, with at least one transition between an outer surface and the innermost layer 320. For example, the hardness and/or refractive index of each layer can progressively increase from the outermost layer to the inner most layer. The outermost layer 305 that is proximate to the capsular bag can have a refractive index of approximately 1.38 and can have a hardness characteristic that permits it to be easily deformed by a small amount of ocular force. The refractive index and the hardness characteristic can progressively increase such that the inner most layer 320 has a refractive index of approximately 1.41 and has a higher hardness characteristic than the outermost layer 305 such that it is deformed less or not at all by the maximum ocular force exerted by the capsular bag. The refractive index and/or the hardness characteristic of the layers 310 and 315 can be greater than the refractive index and the hardness characteristic of the outermost layer 305. The refractive index and/or the hardness characteristic of the layers 310 and 315 can be less than the refractive index and the hardness characteristic of the innermost layer 320. The refractive index and/or the hardness characteristic of the second inner layer 315 can be greater than the refractive index and the hardness characteristic of the first inner layer 310.

Figure 3A:
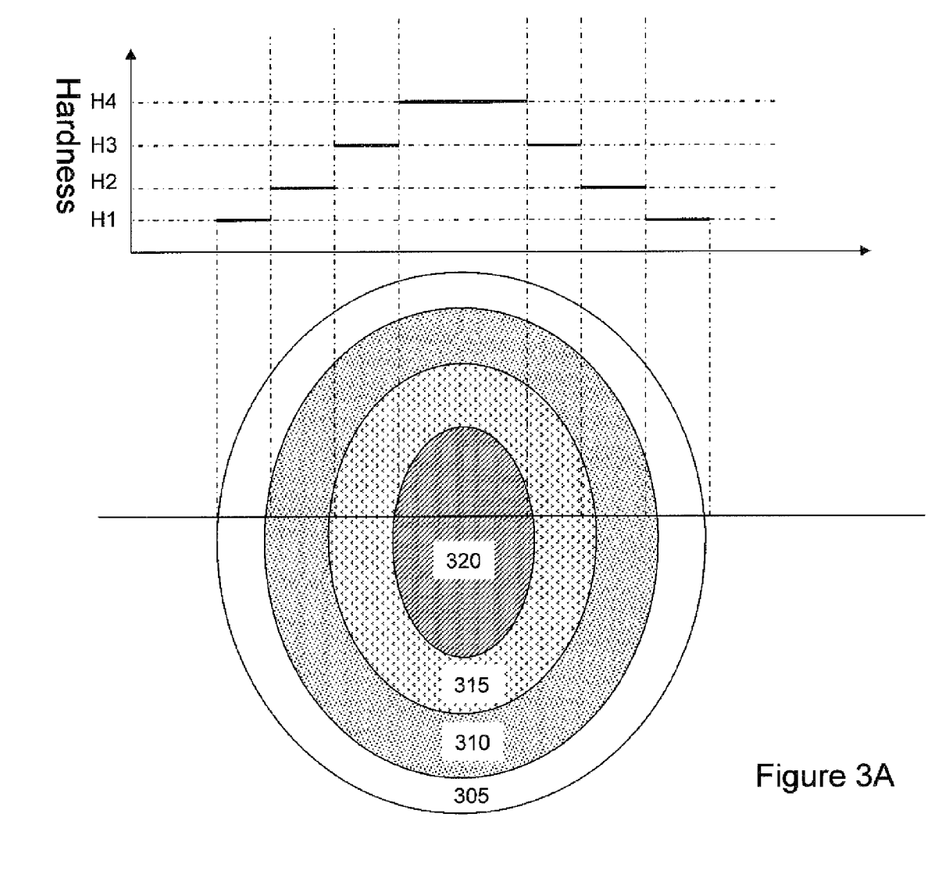
FIGS. 3A and 3B illustrate different hardness profiles for various implementations of the optic illustrated in FIG. 2B.
Figure 3B:
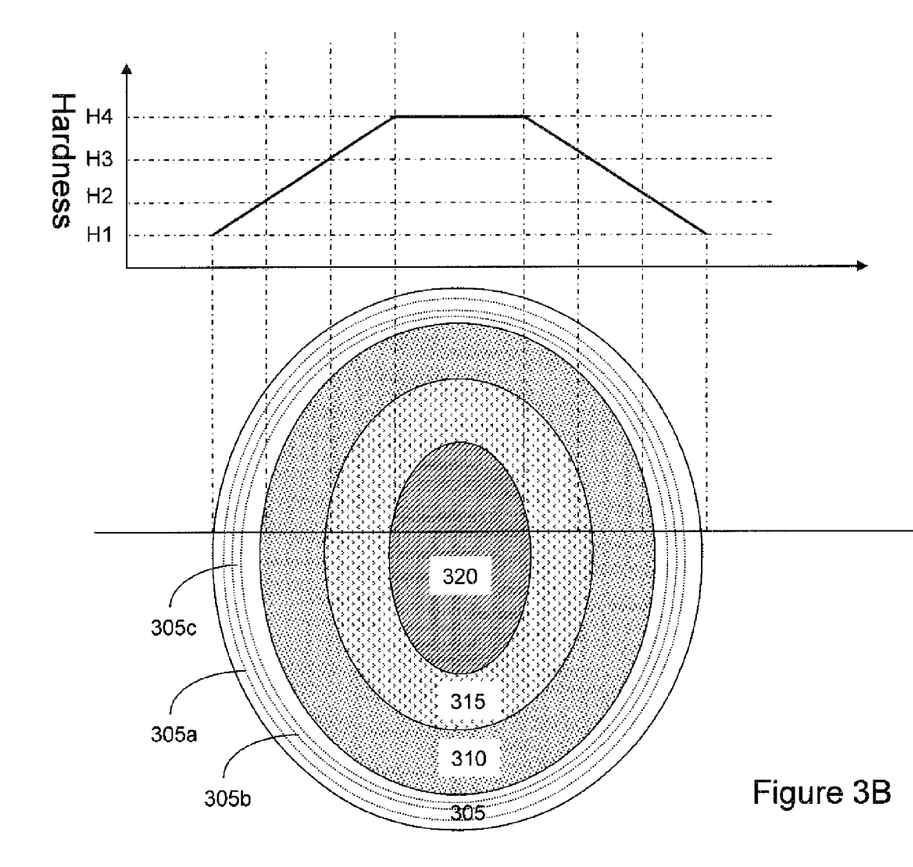

FIGS. 3A and 3B illustrate two different hardness profiles for various implementations of the optic 28. In the hardness profile illustrated in FIG. 3A, the outermost layer 305 has a hardness characteristic H1 that is substantially uniform across the width of the outermost layer 305. The first inner layer 310 has a hardness characteristic H2 that is substantially uniform across the width of the first inner layer 310. The hardness characteristic H2 preferably is greater than the hardness characteristic H1. The second inner layer 315 has a hardness characteristic H3 that preferably is greater than H2. In the second inner layer 315, the hardness characteristic can be substantially uniform across the width of the second inner layer 315. The innermost layer 320 can have a hardness characteristic that is substantially uniform across the width of the innermost layer 320. In various implementations, the hardness H4 of the innermost layer 320 can be greater than the hardness H3 of the second inner layer 315 or other layers 305 and 310. In one implementation, the hardness characteristic can be discontinuous across the boundary of the adjacent layers as illustrated in FIG. 3A. In various implementations, layers of material having a hardness characteristic that is between the hardness characteristics of two adjacent layers may be provided between two adjacent layers to reduce the discontinuity in the hardness profile.

In the hardness profile illustrated in FIG. 3B, the outermost layer 305 has a hardness characteristic that increases from a value H1 to a value H2 across the width of the anterior portion of the outermost layer 305. The increase is gradual between the outer and inner portions of the outermost layer 305. In the illustrated embodiment, the gradual increase is linear. The first inner layer 310 has a hardness characteristic that increases gradually, e.g., linearly, from a value H2 to a value H3 across the width of the anterior portion of the first inner layer 310. The second inner layer 315 has a hardness characteristic that increases gradually, e.g., linearly, from a value H3 to a value H4 across the width of the anterior portion of the second inner layer 315. The innermost layer 320 has a hardness characteristic H4 that is substantially constant across the width of the innermost layer 320. In various implementations, the hardness characteristic H4 of the innermost layer can vary (e.g. linearly) across the width of the innermost layer 320. FIG. 3B also illustrates embodiments where the hardness characteristic varies within the optic without substantial discontinuities between adjacent zones or portions. Hardness profiles having either the hardness value or the slope of the hardness profile being substantially continuous across adjacent zones or portions may be advantageous to allow a continuous deformation of the optic 28 such that the image produced by the optic 28 is aberration free in the entire accommodation range.

In one example method, to achieve substantially continuously varying, e.g., linearly increasing, hardness profile as illustrated in FIG. 3B, at least some layers can include a base material that is doped with a dopant that can affect the hardness. The doping process can be adjusted to achieve a desired hardness profile.

In another example method, at least some of the layers (for example 305) can include multiple sub-layers (for example, 305a, 305b and 305c), each sub-layer having a progressively increasing hardness characteristic by any suitable technique. The number of sub-layers, the thickness of each sub-layer and the hardness characteristic of each sub-layer can be adjusted to achieve non-discontinuous, e.g., gradually varying and in some cases approximately linearly increasing, hardness profile for each layer.

Figure 4A:
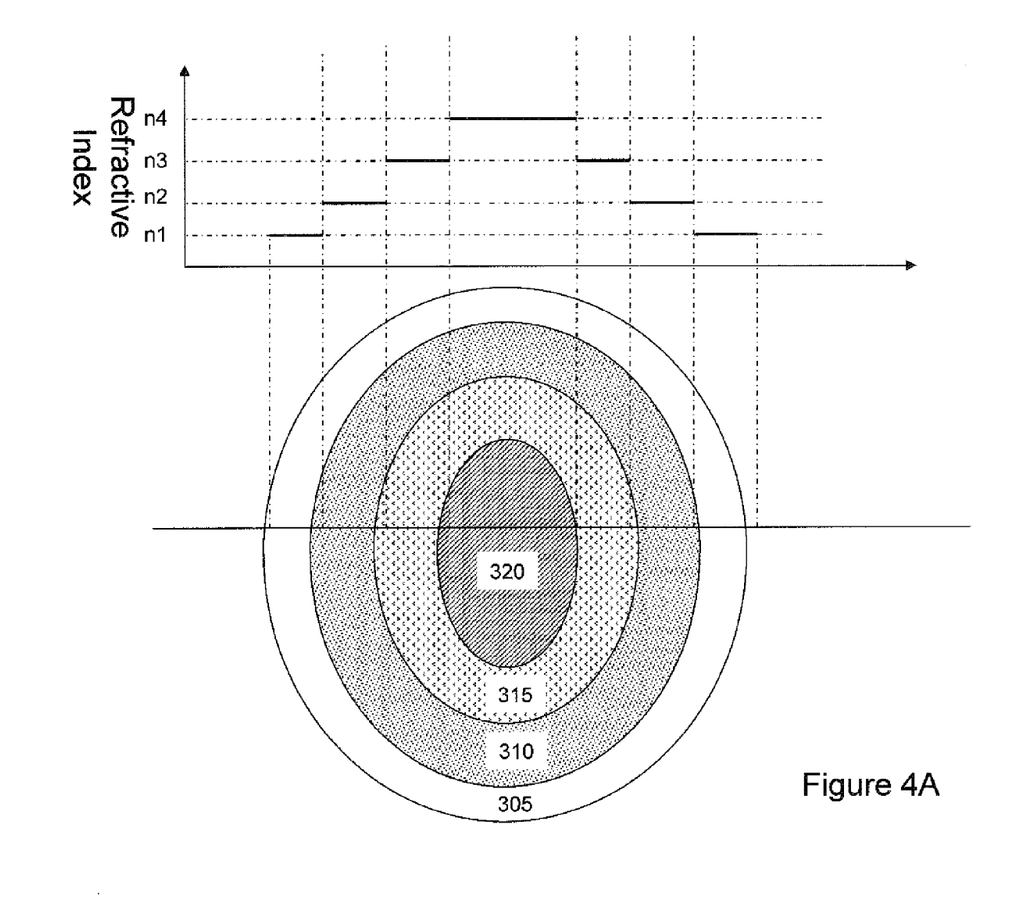
FIGS. 4A and 4B illustrate different refractive index profiles for various implementations of the optic illustrated in FIG. 2B.
Figure 4B:
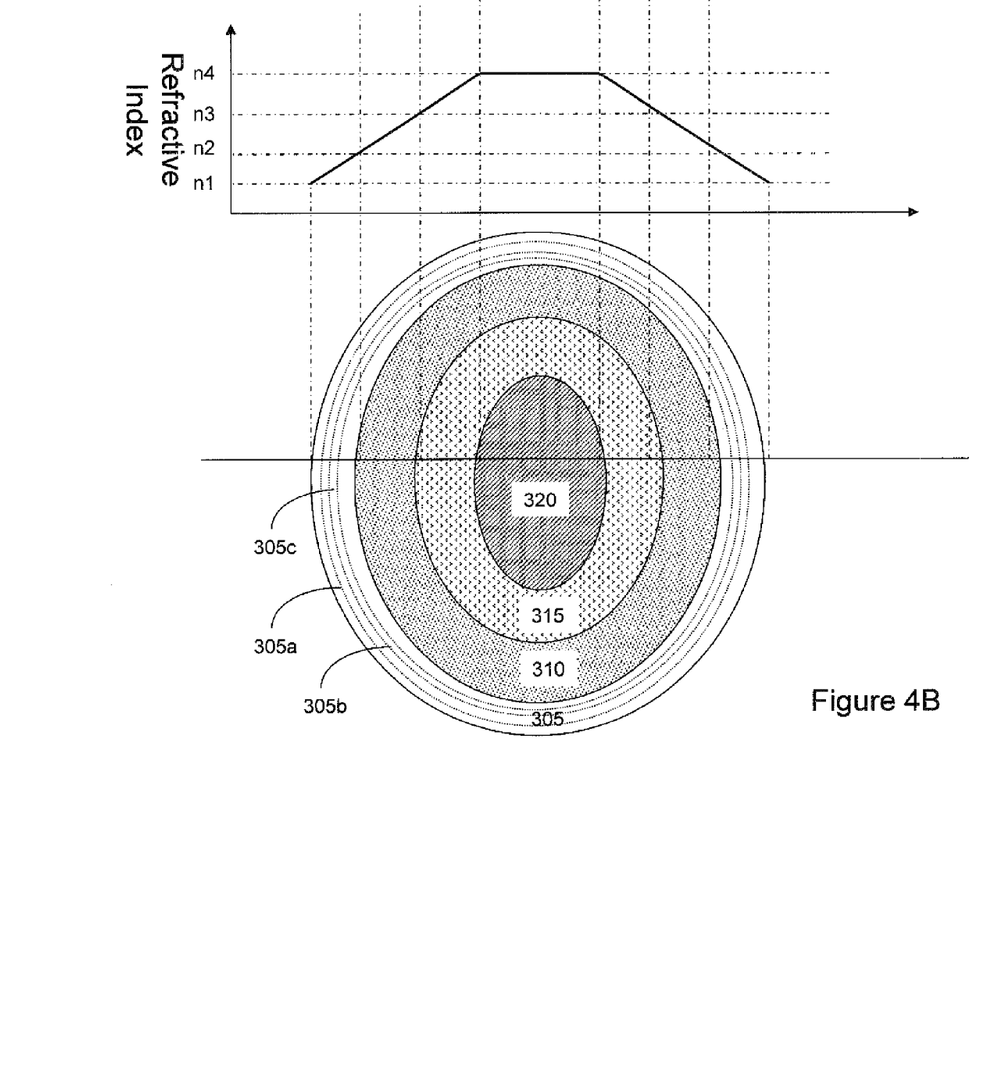
Figure 5:
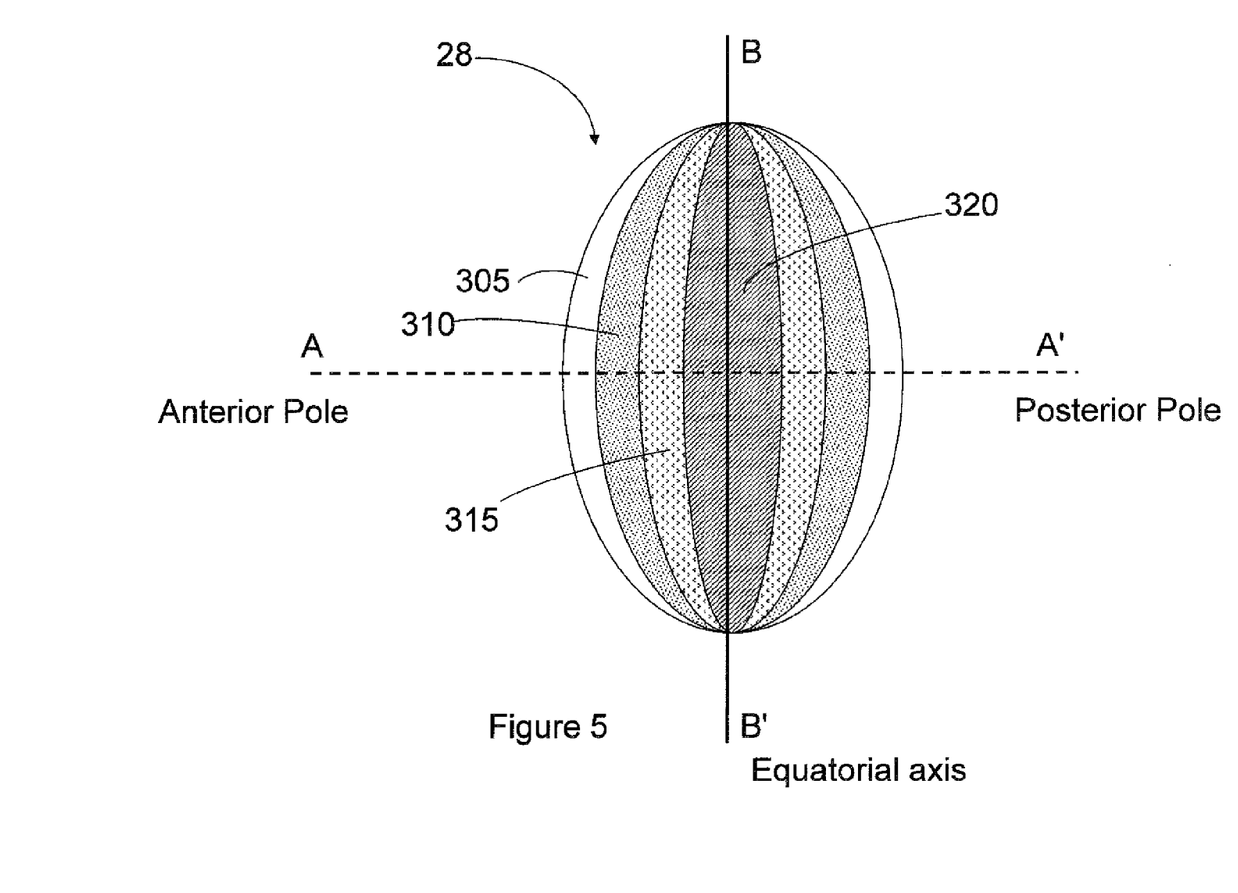
FIG. 5 is a cross-sectional view of an implementation of an optic including a plurality of layers with progressively increasing hardness and/or refractive characteristic that are joined in a region disposed around the equatorial axis.
Figure 6A:
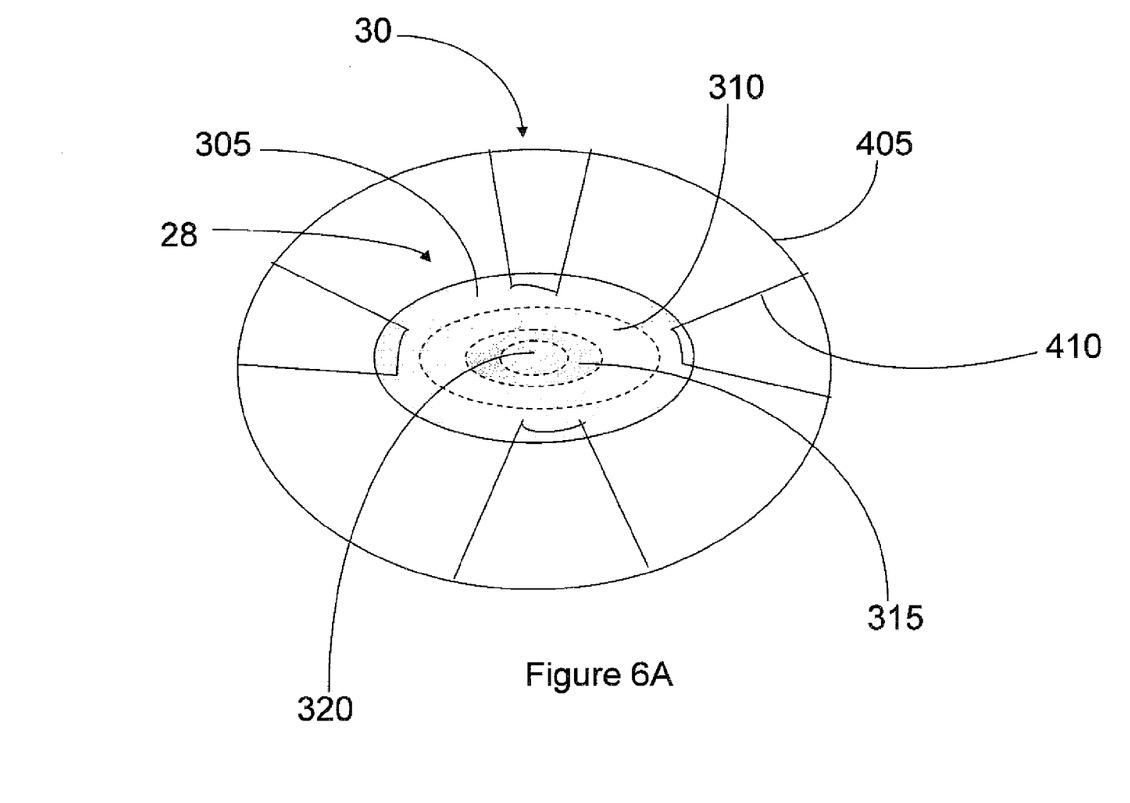
FIG. 6A is a top view of an implementation of an intraocular lens which includes a plurality of layers with progressively increasing hardness and/or refractive characteristic connected to a haptic structure.
Figure 6B:
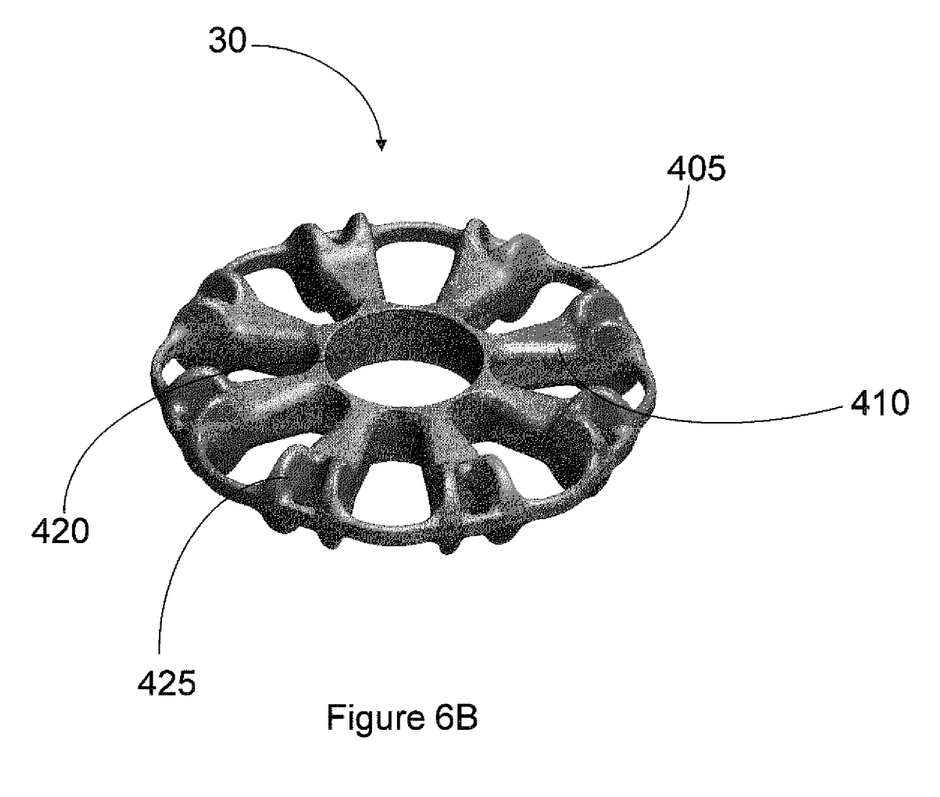
FIG. 6B is a top view of an implementation of a haptic that can be connected to an implementation of an intraocular lens which includes a plurality of layers with progressively increasing hardness and/or refractive characteristic.

FIGS. 4A and 4B illustrate different refractive index profiles for various implementations of the optic illustrated in FIG. 2B. In the refractive index profile illustrated in FIG. 4A, the outermost layer 305 has a refractive index n1 that is substantially uniform across the width of the outermost layer 305. The first inner layer 310 has a refractive index n2 that is substantially uniform across the width of the first inner layer 310. In various implementations, the refractive index n2 of the first inner layer 310 can be greater than the refractive index of the outermost layer 305. The second inner layer 315 can have a refractive index n3 that is substantially uniform across the width of the second inner layer 315. In various implementations, the refractive index n3 of the second inner layer 315 can be greater than the refractive index n2 of the first inner layer 310. The innermost layer 320 has a refractive index n4 that can be substantially uniform across the width of the innermost layer 320. The refractive index n4 of the innermost layer 320 can be greater than the refractive index n3 of the second inner layer 315 and/or any of the other layers 305 and 310. Similar to the hardness profile illustrated in FIG. 3A, the refractive index characteristic is discontinuous at the boundary between the various layers. In various implementations, layers of material having a refractive index that is between the refractive index of two adjacent layers may be provided between two adjacent layers for the purpose of index matching and to reduce the discontinuity in the refractive index profile.

In the refractive index profile illustrated in FIG. 4B, the outermost layer 305 has a refractive index characteristic that increases from a value n1 to a value n2 across the width of the anterior portion of the outermost layer 305. The increase is gradual between the outer and inner portions of the outermost layer 305. In the illustrated embodiment, the gradual increase is linear. The first inner layer 310 has a refractive index that gradually (e.g. linearly) increases from a value n2 to a value n3 across the width of the anterior portion of the first inner layer 310. The second inner layer 315 has a refractive index that increases gradually (e.g. linearly) from a value n3 to a value n4 across the width of the anterior portion of the second inner layer 315. The innermost layer 320 has a refractive index n4 that is constant across the width of the innermost layer 320. In various implementations, the refractive index of the innermost layer 320 can vary across the width of the innermost layer 320. Refractive index profiles having either the value of the refractive index or the slope of the index profile being substantially continuous across adjacent zones or portions may be advantageous in reducing optical aberrations and distortions in the image produced by the optic 28.

In various implementations, the refractive index of the plurality of layers 305, 310, 315 and 320 can vary between approximately 1.0 and 1.6. In various implementations, the hardness characteristic of the plurality of layers 305, 310, 315 and 320 can vary between a Young's modulus of approximately 20 kpa and 1000 kpa, with the soft layers preferably less than 100 kpa, and the stiff layers 500 kpa or greater.

In another embodiment, the refractive index and/or hardness characteristic can progressively decrease from the outer to inner layers. In another embodiment, the refractive index and/or hardness characteristic may initially increase and then decrease moving from the outer to inner layers. In another embodiment, the refractive index and/or hardness characteristic may initially decrease and then increase moving from the outer to inner layers.

In various implementations, the optic 28 can be deformed asymmetrically to correct for astigmatism. For example, the optic 28 can be configured such that, in response to an ocular force, the portion of the optic 28 above (or forward of) the optical axis A-A' can deform to a larger or smaller extent than the portion of the optic 28 below (or rearward of) the optical axis A-A'. In various implementations, the optic 28 can be configured such that, in response to an ocular force, the anterior portion 27 of the optic 28 can deform to a larger or smaller extent than the posterior portion 29 of the optic 28. In various implementations, the hardness characteristic of the various layers 305, 310, 315 and 320 can be adjusted (for example, by doping different layers or different portions of one layer) such that varying amounts of deformation can be obtained in different meridional planes in response to ocular force.

The optic 28 can be formed by suitable methods, such as molding, casting, and/or dip-coating. In one implementation, the innermost layer 320 may be manufactured first and each subsequent layer (315, 310 and 305 in that order) may be molded on the innermost layer 320. In various implementations, each layer may be coated with an anti-reflection coating to reduce optical aberrations and/or distortions. In various implementations, interleaving layers such as diffractive layers, index matching layers, etc may be disposed between the various layers.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An accommodating intraocular lens (IOL), comprising:
   an outer lens enclosure having an anterior structure comprising an anterior surface configured to reside adjacent an interior anterior surface of an evacuated capsular bag and a posterior structure comprising a posterior surface configured to reside adjacent to an interior posterior surface of the evacuated capsular bag, the anterior surface and the posterior surface of the outer lens enclosure extending to and being joined at an equatorial zone of the intraocular lens;
   a first inner core within the outer lens enclosure, the first inner core having an anterior zone and a posterior zone, the anterior and posterior zones of the first inner core being disposed adjacent to the outer lens enclosure;
   a second inner core within the first inner core, the second inner core having an anterior zone and a posterior zone, the anterior and posterior zones of the second inner core being adjacent to the first inner core; and
   an innermost core within the second inner core and disposed between the anterior zone and the posterior zone of the second inner core;
   wherein the intraocular lens is deformable by ciliary muscle action when positioned in the evacuated capsular bag such that at least the outer lens enclosure, the first inner core, or the second inner core are deformed by progressively increasing ocular force, the intraocular lens having an unaccommodated state in which the intraocular lens provides a base optical power and an accommodated state in which the outer lens enclosure and the first inner core, and the second inner core each provide an add power,
   wherein the hardness of each of the outer lens enclosure, first inner core, second inner core, and innermost core progressively decrease from the outer lens enclosure to the innermost core,
   wherein the refractive index of each of the outer lens enclosure, first inner core, second inner core, and innermost core progressively decrease from the outer lens enclosure to the innermost core,
   wherein the innermost core comprises a material that is more deformable than a material of at least one of the first inner core, the second inner core, and the outer lens enclosure,
   wherein the outer lens enclosure, the first inner core, the second inner core, and the innermost core each provide up to 1 diopter of add power in the fully accommodated state,
   wherein the outer lens enclosure, the first inner core, the second inner core, and the innermost core are arranged concentrically within the IOL as gradually reducing spheres within the internal volume of the IOL.

2. The accommodating intraocular lens of claim 1, wherein the innermost core comprises a refractive index that is lower than a refractive index of at least one of the first inner core, the second inner core and the outer lens enclosure.

3. The accommodating intraocular lens of claim 2, wherein each of the zones anterior and posterior to the innermost core comprises a higher refractive index than the innermost core and the outer lens enclosure comprises an index of refraction that is more than at least one of the zones of the first or second inner cores.

4. The accommodating intraocular lens of claim 1, wherein index of refraction and hardness of at least two of the outer lens enclosure, the first inner core and the second inner core vary within the intraocular lens.

5. The accommodating intraocular lens of claim 1, wherein:
   an interface is provided within the outer lens enclosure and an antireflective coating is disposed on said interface.

* * * * *